(12) United States Patent
Pope et al.

(10) Patent No.: US 7,821,635 B2
(45) Date of Patent: *Oct. 26, 2010

(54) IN-SITU DETECTION AND ANALYSIS OF METHANE IN COAL BED METHANE FORMATIONS WITH SPECTROMETERS

(76) Inventors: John Pope, 1166 N. 11th St., Laramie, WY (US) 82072; John Herries, 715 Ord St., Laramie, WY (US) 82070

( * ) Notice: Subject to any disclaimer, the term of this patent is extended or adjusted under 35 U.S.C. 154(b) by 0 days.

This patent is subject to a terminal disclaimer.

(21) Appl. No.: 10/668,228

(22) Filed: Sep. 24, 2003

(65) Prior Publication Data

US 2004/0061858 A1   Apr. 1, 2004

Related U.S. Application Data

(63) Continuation of application No. 10/266,638, filed on Oct. 9, 2002, now Pat. No. 6,678,050, which is a continuation of application No. PCT/US01/11563, filed on Apr. 11, 2001.

(60) Provisional application No. 60/196,620, filed on Apr. 11, 2000, provisional application No. 60/196,182, filed on Apr. 11, 2000, provisional application No. 60/196,523, filed on Apr. 11, 2000, provisional application No. 60/196,000, filed on Apr. 11, 2000.

(51) Int. Cl.
*G01J 1/04* (2006.01)
*G01N 21/00* (2006.01)
(52) U.S. Cl. .................... 356/326; 356/436
(58) Field of Classification Search ......... 356/432–437, 356/441, 319, 326; 250/256, 269.1, 339.11, 250/341.8
See application file for complete search history.

(56) References Cited

U.S. PATENT DOCUMENTS

| 3,947,683 | A | | 3/1976 | Schultz et al. |
| 4,066,892 | A | * | 1/1978 | Givens ................. 376/165 |
| 4,802,761 | A | | 2/1989 | Bowen et al. |

(Continued)

OTHER PUBLICATIONS

A. R. Smits et al., "In-Situ Optical Fluid Analysis as an Aid to Wireline Formation Sampling" SPE Formation Evaluation, Jun. 1995, pp. 91-98.

*Primary Examiner*—Gregory J. Toatley, Jr.
*Assistant Examiner*—Sang H. Nguyen
(74) *Attorney, Agent, or Firm*—William G. Ackerman (57) ABSTRACT

A measuring system for in-situ measurements down a well (1) by a spectrometer (4) is provided. The spectrometer (4) includes a radiation source (5) and a detector (6). A probe (15) optically connected to the spectrometer (4) and includes an optical pathway (7) for transmission of a radiation from the radiation source (5) and at least a second optical pathway for transmission of a characteristic radiation from a sample to the detector (6). A positioner is provided to position the probe (15) near a side surface (11) of the borehole (3) and to optically couple the optical pathways (7) to the side surface (11), wherein the probe (15) is traversable up and down the well (1) by way of a guide operatively connected to the probe (15) and to a fixed location at the wellhead. By use of the apparatus and method a concentration of methane or other substance of interest is obtained, and thereby, a potential production of a coal bed methane formation is obtained.

73 Claims, 4 Drawing Sheets

U.S. PATENT DOCUMENTS

| | | |
|---|---|---|
| 4,892,383 A | 1/1990 | Klainer et al. |
| 4,994,671 A | 2/1991 | Safinya et al. |
| 5,166,747 A | 11/1992 | Schroeder et al. |
| 5,167,149 A | 12/1992 | Mullins et al. |
| 5,225,674 A | 7/1993 | Frantz et al. |
| 5,293,931 A | 3/1994 | Nichols et al. |
| 5,331,156 A | 7/1994 | Hines et al. |
| 5,462,116 A | 10/1995 | Carroll |
| 5,526,110 A | 6/1996 | Braymen |
| 5,859,430 A | 1/1999 | Mullins et al. |
| 5,939,717 A | 8/1999 | Mullins |
| 6,268,911 B1 | 7/2001 | Tubel et al. |
| 6,350,986 B1 | 2/2002 | Mullins et al. |
| 6,355,928 B1 | 3/2002 | Skinner et al. |
| 6,388,251 B1 | 5/2002 | Papanyan |
| 6,507,401 B1 | 1/2003 | Turner et al. |

* cited by examiner

IN-SITU DETECTION AND ANALYSIS OF METHANE IN COAL BED METHANE FORMATIONS WITH SPECTROMETERS

CROSS REFERENCE TO RELATED APPLICATIONS

This application is a continuation of International Patent Application No. PCT/US01/11563, filed Apr. 11, 2001, designating the United States of America, and published as WO 01/77628, the entire disclosure of which is incorporated herein by reference. Priority is claimed based on Provisional Application Nos. 60/196,620, 60/196,182, 60/196,523 and 60/196,000 filed Apr. 11, 2000.

TECHNICAL FIELD

This invention relates to in-situ methods of measuring or analyzing dissolved, free, or embedded substances with a spectrometer and an apparatus to carry out the method. In particular this invention relates to a method and apparatus of analyzing substances down a well. More particularly, this invention relates to a method and apparatus to detect, analyze and measure methane or related substances in subsurface coal bed formations using a portable optical spectrometer to thereby predict a potential methane production of the well.

BACKGROUND AND SUMMARY OF THE INVENTION

Coal bed methane is methane that is found in coal seams. Methane is a significant by-product of coalification, the process by which organic matter becomes coal. Such methane may remain in the coal seam or it may move out of the coal seam. If it remains in the coal seam, the methane is typically immobilized on the coal face or in the coal pores and cleat system. Often the coal seams are at or near underground water or aquifers, and coal bed methane production is reliant on manipulation of underground water tables and levels. The underground water often saturates the coal seam where methane is found, and the underground water is often saturated with methane. The methane may be found in aquifers in and around coal seams, whether as a free gas or in the water, adsorbed to the coal or embedded in the coal itself.

Methane is a primary constituent of natural gas. Recovery of coal bed methane can be an economic method for production of natural gas. Such recovery is now pursued in geologic basins around the world. However, every coal seam that produces coal bed methane has a unique set of reservoir characteristics that determine its economic and technical viability. And those characteristics typically exhibit considerable stratigraphic and lateral variability.

In coal seams, methane is predominantly stored as an immobile, molecularly adsorbed phase within micropores of the bulk coal material. The amount of methane stored in the coal is typically termed the gas content.

Methods of coal bed methane recovery vary from basin to basin and operator to operator. However, a typical recovery strategy is a well is drilled to the coal seam, usually a few hundred to several thousand feet below the surface; casing is set to the seam and cemented in place in order to isolate the water of the coal from that of surrounding strata; the coal is drilled and cleaned; a water pump and gas separation device is installed; and water is removed from the coal seam at a rate appropriate to reduce formation pressure, induce desorption of methane from the coal, and enable production of methane from the well.

Assessment of the economic and technical viability of drilling a coal bed methane well in a particular location in a particular coal seam requires evaluation of a number of reservoir characteristics. Those characteristics include the gas content and storage capability of the coal; the percent gas saturation of the coal; the gas desorption rate and coal density, permeability, and permeability anisotropy; and gas recovery factor.

While industry has developed methods to enhance production from formations that exhibit poor physical characteristics such as permeability and density, currently no practical methods are available to increase the gas content of a coal seam. Thus, identifying coal seams that contain economic amounts of methane is a critical task for the industry. The primary issue in identifying such coal seams involves developing a method and apparatus to quickly and accurately analyze coal seams for gas content.

Currently accepted methods of measuring gas content involve extracting a sample of the coal from the seam and measuring the amount of gas that subsequently desorbs, either by volume or with a methane gas sensor. However, collection of the coal sample usually changes its gas content to a significant extent before gas desorption is monitored. This degradation of sample integrity leads to degradation of the data collected. That degradation of data creates significant doubt in the results of those common methods. As well, because these methods hinge on waiting for the methane to desorb from the coal, they require inordinate amounts of time and expense before the data is available.

Downhole sensing of chemicals using optical spectroscopy is known for oil wells. For example, Smits et. al., "In-Situ Optical Fluid Analysis as an Aid to Wireline Formation Sampling", 1993 SPE 26496, developed an ultraviolet/visible spectrometer that could be placed in a drill string. That spectrometer was incorporated in a formation fluid sampling tool whereby formation fluids could be flowed through the device and analyzed by the spectrometer. That spectrometer was largely insensitive to molecular structure of the samples, although it was capable of measuring color of the liquids and a few vibrational bond resonances. The device only differentiates between the O—H bond in water and the C—H bond in hydrocarbons and correlates the color of the analyte to predict the composition of the analyte. The composition obtained by the device is the phase constituents of the water, gas and hydrocarbons. By correlating observation of gas or not gas with observation of water, hydrocarbon, and/or crude oil, the instrument can distinguish between separate phases, mixed phases, vertical size of phases, etc. By correlating the gas, hydrocarbon, and crude oil indicators, the instrument can presumably indicate if a hydrocarbon phase is gaseous, liquid, crude, or light hydrocarbon. A coal bed methane well with varying hydrocarbons from coal to methane and, possibly, bacterial material, provides an environment too complex for such a device to differentiate methane and the other substances of interest. The device is not capable of resolving signals from different hydrocarbons to a useful extent, and the device is not capable of accurate measurements needed for coal bed methane wells. Furthermore, the requirements that the sample be fluid, that analysis occur via optical transmission through the sample, and that the sample be examined internal to the device precludes its use for applications such as accurately measuring gas content of coal seams.

In other apparatuses known in U.S. Pat. No. 4,802,761 (Bowen et. al.) and U.S. Pat. No. 4,892,383 (Klainer, et. al.), a fiber optic probe is positioned to transmit radiation to a chemically filtered cell volume. Fluid samples from the surrounding environment are drawn into the cell through a membrane or other filter. The fiber-optic probe then provides an optical pathway via which optical analysis of the sample volume can be affected. In the method from Bowen et. al., a Raman spectrometer at the wellhead is used to chemically analyze the samples via the fiber optic probe. The method allows purification of downhole fluid samples using chromotographic filters and subsequent analysis of the fluid and its solutes using Raman spectroscopy. However, the stated requirement that the Raman spectrometer be remote from the samples of interest and that it employ fiber-optic transmission devices for excitation and collection ensures that the sensitivity of the device is limited. The device further does not consider the conditions present in subsurface wells when analyzing the samples. Furthermore, as in the Smits et. al. case, the requirements in Bowen et. al. and Klainer et. al. that the sample be fluid and that the sample be examined internal to the device significantly decrease the utility of the device for applications such as measuring gas content of coal seams.

Methods of sample preparation and handling for well tools have been described, as well. In U.S. Pat. No. 5,293,931 (Nichols et. al.), an apparatus is disclosed for isolating multiple zones of a well bore. The isolation allows isolated pressure measurements through the well bore or wellhead collection of samples of fluids from various positions in the wellbore. However, such wellhead sample collection degrades sample integrity and does not provide a practical method or apparatus for assessment of gas content in coal seams. The apparatus shown significantly affects any sample collected and is basically a collection device set down a well.

An object of the invention is to provide a method and system to accurately measure substances in wells using optical analysis.

Another object of the invention is to provide a method and measuring system capable of measuring methane in a coal bed methane well.

Another object of the invention is to provide a method and measuring system which utilizes a spectrometer to analyze methane and other substances with emitted, reflected or scattered radiation from the substances and thereby allow a measurement of a side surface of the well.

Another object of the invention is to provide a method and measuring system to accurately measure a concentration of methane in a coal bed methane well and calculate a concentration versus depth for a single well and calculate concentrations versus depth for other wells to thereby predict a potential production of a coal bed methane field.

The objects are achieved by a measuring system for introduction into a well with a housing traversable up and down the well, a guide extending down the well from a fixed location and being operatively connected to the housing, a spectrometer being located inside the housing and including a radiation source, a sample interface to transmit a radiation from the radiation source to a sample, and a detector to detect a characteristic radiation emitted, reflected or scattered from the sample and to output a signal, and a signal processor to process the signal from the detector and calculate a concentration of a substance in the sample.

Another aspect of the invention is a measuring system for in-situ measurements down a well by a spectrometer. The spectrometer includes a radiation source and a detector. A probe is provided optically connected to the spectrometer and including an optical pathway for transmission of a radiation from the radiation source and at least a second optical pathway for transmission of a characteristic radiation from a sample to the detector. A positioner is provided to position the probe near a side surface of the borehole and to optically couple the optical pathways to the side surface of the borehole, wherein the probe is traversable up and down the well by way of a guide operatively connected to the probe and to a fixed location at the wellhead.

Another aspect of the invention is a method of measuring methane in at least one coal bed methane well. An instrument package is provided in a housing, and the housing is lowered a distance down the well. A radiation source is positioned to irradiate a sample, and a detector is positioned to detect the characteristic radiation from the interaction between the sample and the incident radiation from the radiation source. The sample is irradiated to produce the characteristic radiation. The concentration of methane in the sample is measured by detecting the characteristic radiation with the detector. The detector transmits a signal representative of the concentration of methane to a signal processor, and the signal processor processes the signal to calculate the concentration of methane in the sample.

In another aspect of the invention, a method of measuring a side surface of a borehole using optical spectrometers is provided. An optical spectrometer with a radiation source and a detector is provided. The side surface of the borehole is optically connected to the radiation source and the detector. The radiation source irradiates the side surface of the borehole, and the emitted, reflected or scattered characteristic radiation from the side surface of the borehole is collected. The collected characteristic radiation is transmitted to the detector to output or produce a signal. The signal is transmitted to a signal processor and the concentration of a substance on the side surface of the borehole is calculated.

The side surface is usually a solid material such as coal, sandstone, clay or other deposit. The side surface has been affected by the drill bit. The side surface may also have a film of drilling "mud" or some other contaminant (introduced or naturally found) that has been distributed by the drill bit. The measurement system analyzes the surface of that material, or the material is penetrated to analyze its interior. The surface may be treated (i.e. by washing it with water) before being analyzed. The material of interest is characterized along with any other materials adsorbed or absorbed to the material. These could include gases, liquids, or solids. Preferably, the methane adsorbed to the coal surface and in its pores is identified. The amount of methane on the surface and in the pores is measured.

The samples of interest may be a face of the coal seam, the coal itself, a bacterium or bacterial community which may indicate methane, the water in the well, methane entrained in the coal or water, methane dissolved in the water, or free gas. A free gas may be examined in-situ by providing a pressure change to the water or to the coal and collecting the resultant gas by way of a head-space. The sample or substance of interest may be physically, biologically or chemically treated in-situ before measuring to enhance detection or measurement.

The radiation source is of particular concern and is selected depending on the well environment, the substance to be measured and the background of the sample. Coal shows inordinate fluorescence, and often bacteria and other organic material are present near the coal seams. These substances tend to produce fluorescence which interferes with measurements of other substances. Unless the fluorescence is measured, the radiation source and wavelength are selected to minimize these effects. Coal tends to fluoresce between 600 nm and 900 nm with a significant drop in fluorescence under 600 nm. A radiation source which takes into account these ranges is preferred for measuring the methane, especially the methane adsorbed to or embedded in the coal. Thus, the methane signature relative to the other components is maximized. In some instances a signature of the fluorescence is maximized to characterize the methane indirectly.

The measurements lead to establishing a concentration of methane in the coal bed formation and to the potential production or capacity of the coal bed. The methane is analyzed by obtaining through spectrometers a series of spectra representative of scattered, emitted or reflected radiation from methane in the well. The captured spectra are used to determine the concentration at varying depths of methane present in the coal bed formation. The spectra are manipulated and analyzed to produce the concentrations of methane represented in the well. The use of filters which are designed to eliminate or reduce radiation from sources present in the well is needed to accurately determine the methane concentration or other parameters of the coal bed methane well. Other parameters may include a predictor element or compound that is natural or introduced to the coal bed or well. The filters are chosen depending on the chemical which is of interest. Raman spectrometers are used in most testing, however, near infrared lasers and detectors may be employed to avoid the difficulties associated with fluorescence from material or substances in the water or well. The measuring system in this invention is based on high sensitivity. One factor that is used to maintain high sensitivity of the system is the reduction or elimination of moving parts throughout the measuring system.

Other objects, advantages and novel features of the present invention will become apparent from the following detailed description of the invention when considered in conjunction with the accompanying drawings.

DETAILED DESCRIPTION OF THE DRAWINGS

Figure 1:
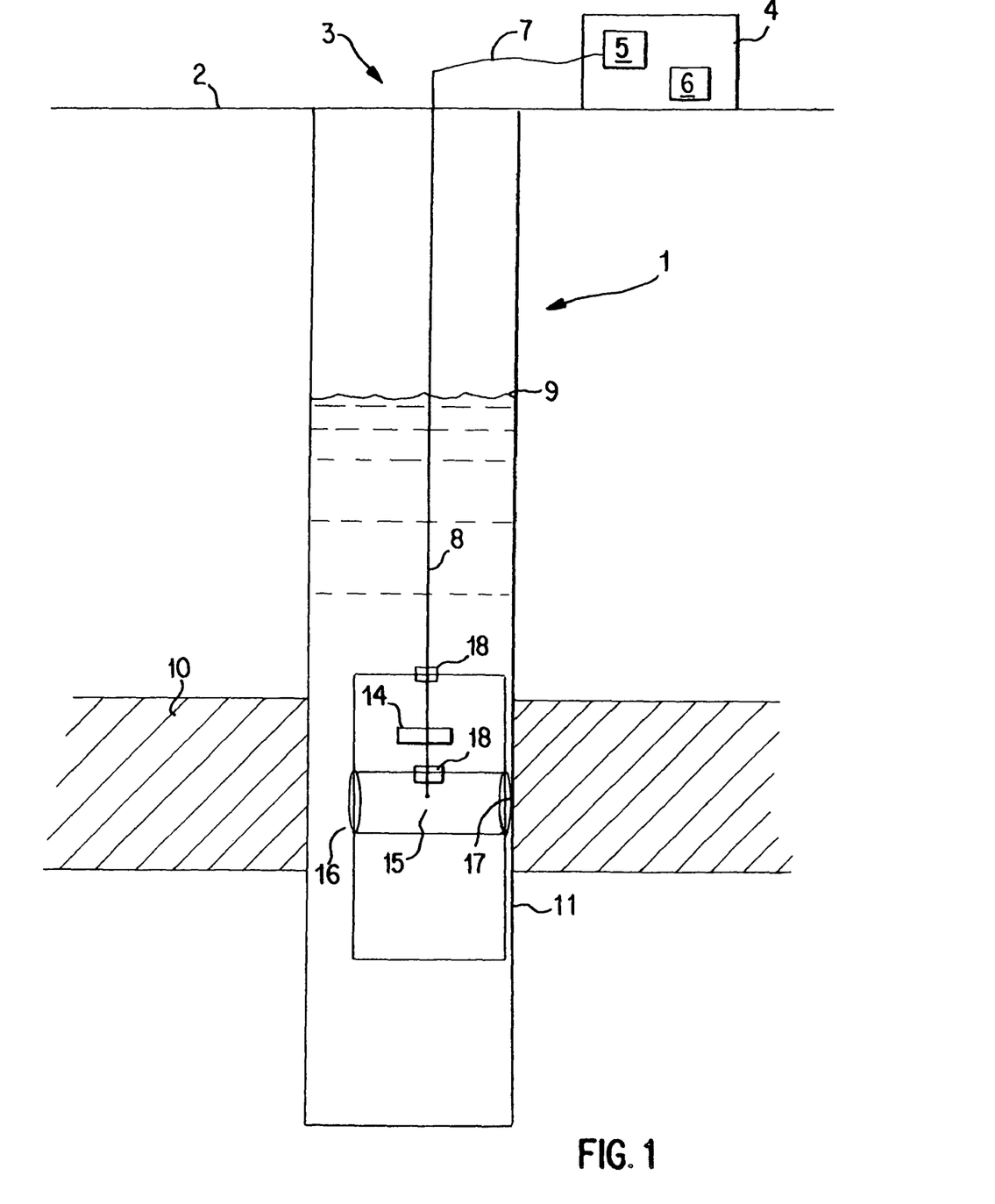
FIG. 1 shows a side plan view of an embodiment of the invention and a coal bed methane well with the spectrometer located at the wellhead and transmission of optical radiation using fibers to a downhole probe.

FIG. 1 shows a coal bed methane well 1 with a borehole 3 extending from a well head to a coal seam 10 with an aquifer fed water level 9. The spectrometer 4 is located at or near the wellhead and includes a radiation source 5 for producing a radiation to transmit down the borehole 3 to a sample interface 25. The radiation from the radiation source is transmitted by way of at least one optical pathway 7. The sample, in this case being water, interacts with the radiation transmitted from the radiation source 5, and a characteristic radiation for the sample is produced by the interaction. The characteristic radiation is then transmitted by an optical pathway 7 to a detector 6 located in the spectrometer 4 at the surface. A suitable optical pathway 7 for transmission is optical fiber 8. Similar elements are represented by the same reference numeral in the drawings.

The optical fiber 8 extends down the borehole 3 to the housing 12 and feeds into the housing through a high-pressure feed-through jacket 18. The jacket 18 allows the fiber 8 to enter the housing 12 without subjecting the housing to the conditions down the well, such as high pressure, particles and the water. The housing protects any filter 14 or other instrumentation enclosed by the housing. The fiber 8 may extend out of the housing through another jacket 18 to optically couple the sample or substance of interest. A tip 15 of the fiber 8 supplies the radiation from the radiation source 5 and collects the characteristic radiation.

The optical fiber 8 may be a bundle of fibers where the center fiber transmits the radiation from the radiation source 5 and the other fibers transmit the characteristic radiation. A single collection fiber for the characteristic radiation may also be used. The fiber 8 may also include a lens. The fibers use a polished tip or fused tip.

The sample interface includes an inlet 16 and an outlet 17 for the water in the well. The water flows into the inlet when the housing is positioned down the well at a depth and flows around the tip 15 of the fiber to thereby interact with the radiation from the radiation source 5.

Figure 2:
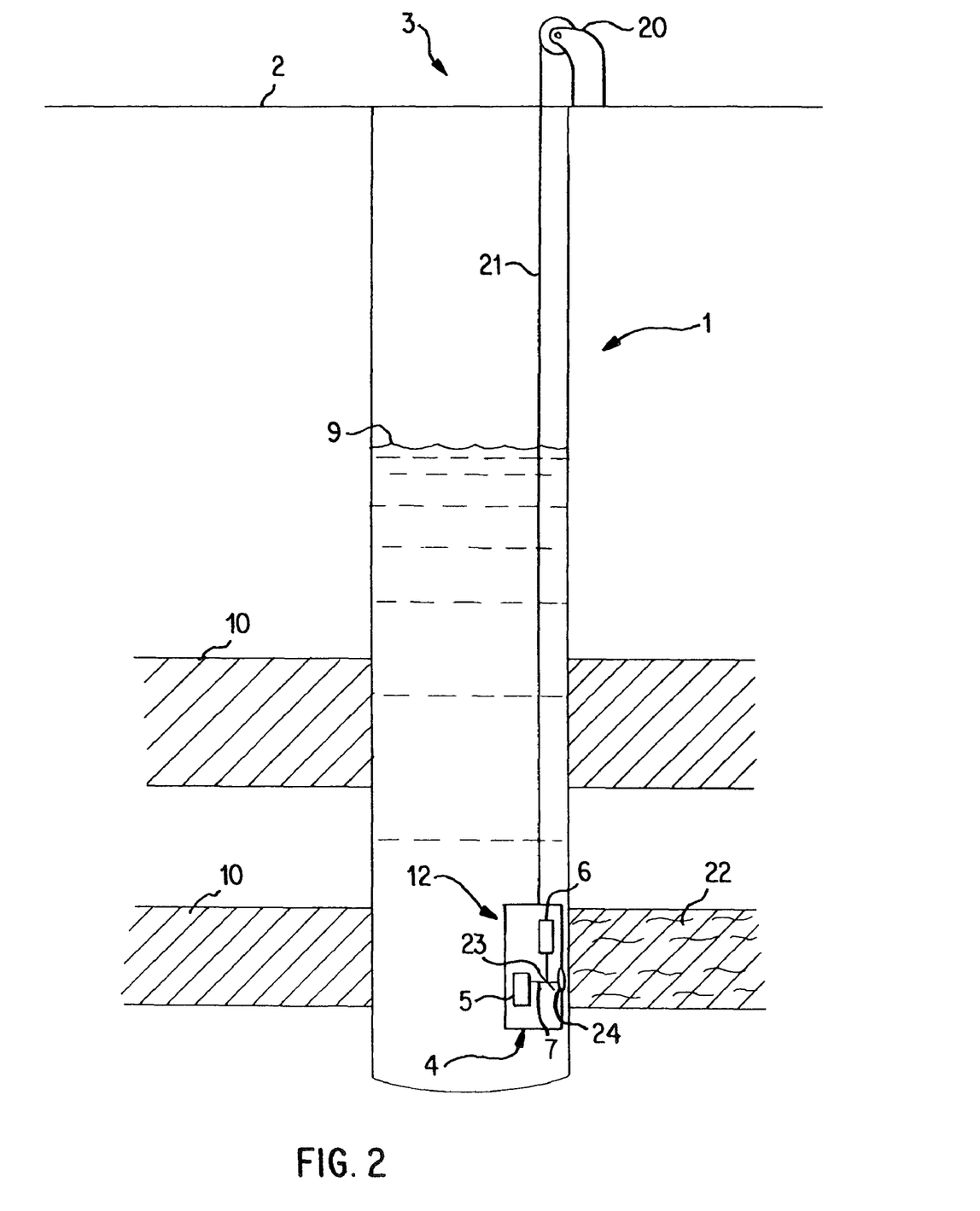
FIG. 2 shows a side plan view of another embodiment of the invention and a coal bed methane well with the spectrometer located in a housing lowered down the well.

In a preferred embodiment shown in FIG. 2, the spectrometer 4 is located down the well 1 in a housing 12, thus reducing the effects of the long distance transmission of the radiation. The spectrometer 4 is lowered down the borehole 3 by a guide wire 21 to a depth, and the depth is controlled by a guide controller 20 at the surface 2.

This embodiment shows the radiation source 5 providing radiation by an optical pathway 7 which is not a fiber. The radiation is directed to a beam splitter 23 and through a window 24 to interact with the sample or substance of interest. The emitted, reflected or scattered radiation is then transmitted through the window 24 into the interior and through the beam splitter 23 to the detector 6.

In this embodiment, no moving parts are present in the housing 12. This allows for increased sensitivity and accuracy.

The guide wire 21 may be a wireline, a slick line, coiled tubing, drill stem or other type of guide. The guide wire is provided for positioning the housing down the well and may also transmit a signal to a data recorder or other processor at the surface. If the signal is not transmitted by the guide wire, a signal or data storage device is needed in the housing. The guide wire may also furnish electrical power to the instrumentation located in the housing, or a battery may be located in the housing.

Figure 3:
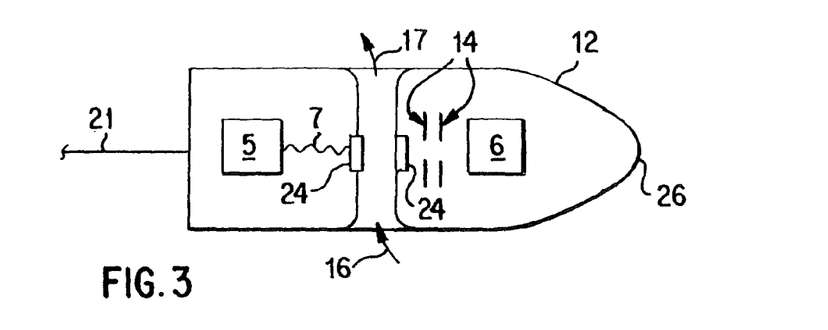
FIG. 3 shows a sectional view of an embodiment of the housing with a flow passage for liquid or gas analysis.

FIGS. 3-6 show embodiments of the housing 12 with the spectrometer 4 enclosed therein, when used with a guide wire 21. FIG. 3 shows a flow passage for the sample interface where the radiation source 5 provides an incident radiation through a window 24 to interact with water. The characteristic radiation is transmitted through another window 24 to the detector 6. The characteristic radiation passes through filters 14 before the detector 6. The housing 12 itself may be streamlined 26 to provide for smooth passage of the housing down the well.

Figure 4:
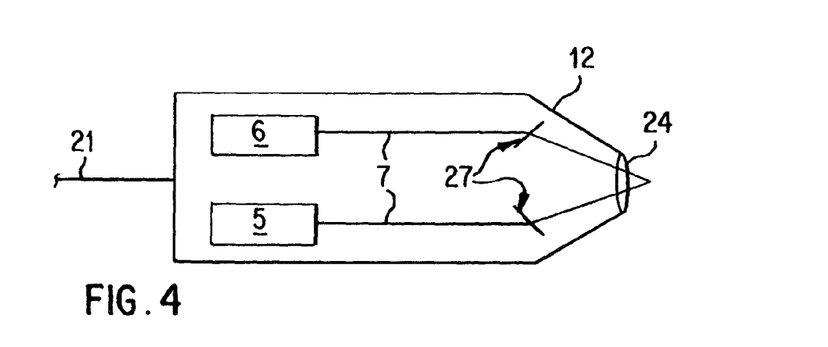
FIG. 4 shows a sectional view of an embodiment of the housing with a non-contacting sample interface.

FIG. 4 shows a housing 12 designed for a non-contacting sample interface at the tip of the housing. Here the radiation source 5 produces radiation which is transmitted by an optical pathway 7 to a reflector or grating 27 to direct the radiation through a window 24 at the tip of the housing. The radiation interacts with the sample or substance of interest a distance away from the window 24. The characteristic radiation is then transmitted through the window 24 and to a reflector or grating 27 to direct the characteristic radiation to the detector 6.

Figure 5:
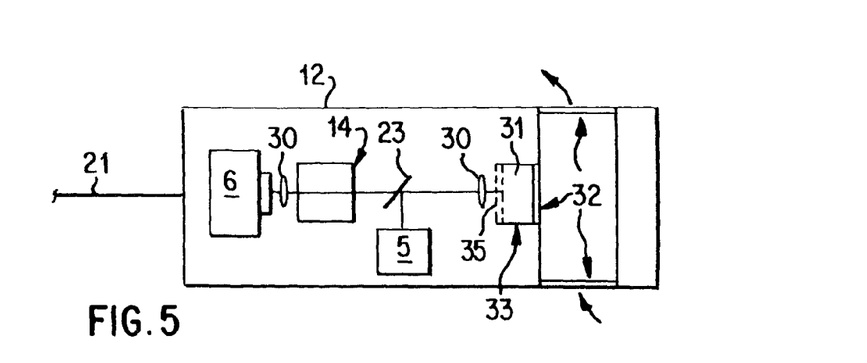
FIG. 5 shows a sectional view of an embodiment of the housing with a head-space for gas analysis.

FIG. 5 shows a confocal arrangement for the housing 12. The radiation source 5 provides radiation directed to a beam splitter 23 which reflects the radiation to a lens 30 and through a window 24 into a head-space 31. The characteristic radiation travels to the beam splitter 23 and to another filter 14 and other lens 30 to the detector 6.

The sample interface includes the head-space 31 which entraps gas produced by a depressurization of water in the flow passage. A plunger 33 or other device is used to depressurize the water. The head-space 31 collects the gas for measurement and analysis. Gates 32 are provided which allow the water to flow into the housing and then isolate the water from the well to allow for depressurization.

Figure 6:
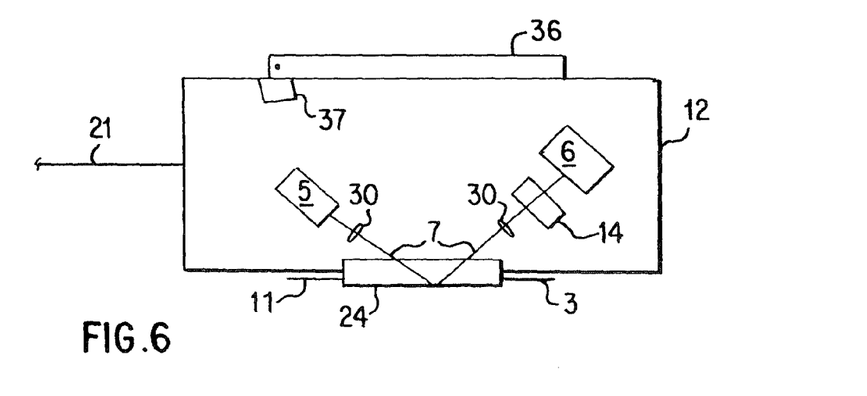
FIG. 6 shows a sectional view of an embodiment of the housing with an off axis sample interface pressing to a side of the borehole.

FIG. 6 shows an off-axis spectrometer 4 configuration. The radiation source 5 is off-axis from the well and face of the borehole 3. The radiation source 5 provides a radiation down an optical pathway 7 through a lens 30 and window 24 onto a sample or substance of interest. The characteristic radiation travels through the window 24, another lens 30 and a filter 14 to the detector 6. The housing 12 has an adjustable device to press the housing to the side surface of the borehole. An extendable leg 36 is provided that by a controller 37 moves out from the housing 12 and contacts the side surface of the borehole opposite the window 24 and thereby moves the housing 12 towards the opposite side of the borehole. The confocal, off axis and non-contacting optics arrangements may be interchanged.

Figure 7:
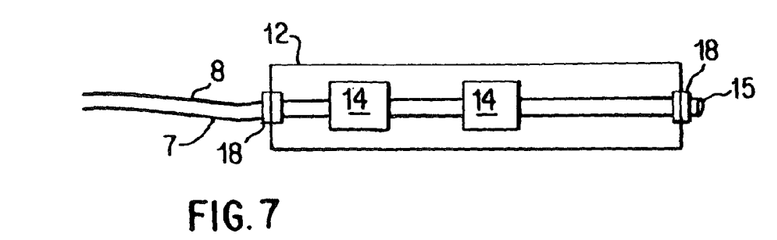
FIG. 7 shows a sectional view of an embodiment of the probe with a fiber optics.

FIGS. 7-11 show embodiments of the housings 12 where fiber optics 8 are employed as at least a portion of the optical pathway 7. FIG. 7 shows a housing 12 as a probe where the spectrometer is not located in the housing. An optical fiber 8 supports the probe and positions the probe along the wellbore. A high-pressure feed-through jacket 18 is used to allow the fiber 8 to enter the housing 12 where filters 14 or other dispersive elements are arranged. The fiber 8 exits the housing and the sample interface is a tip 15 of the fiber 8.

Figure 8:
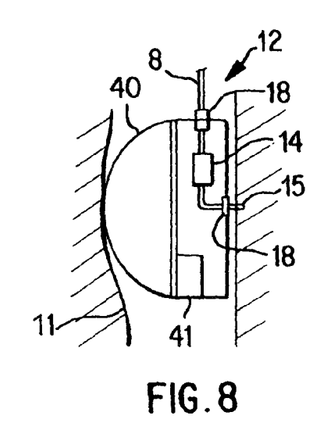
FIG. 8 shows a sectional view of an embodiment of the probe with a sample interface pressed against the side of the borehole.

FIG. 8 shows the use of fiber 8 with an adjustable device for pressing the sample interface against the side surface 11 of the wellbore. A bag 40 is expanded by a controller 41 against the opposite side surface of the borehole to thereby press the tip 15 of the fiber 8 against or into the side surface of the borehole.

Figure 9:
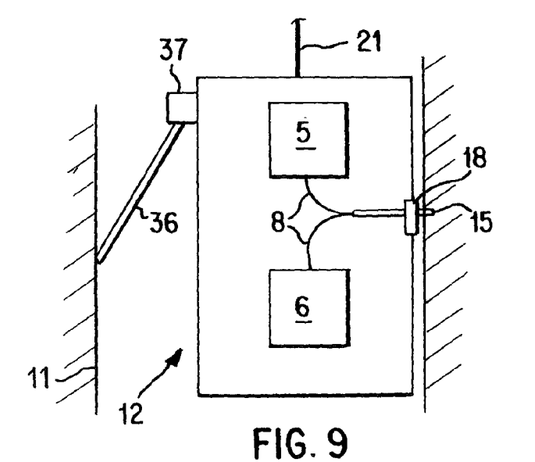
FIG. 9 shows a sectional view of an embodiment of the probe with the spectrometer located downhole and a sample interface as a fiber-optic bundle pressed against the side of the borehole.

FIG. 9 shows the use of fibers where the spectrometer 4 is located in the housing 12. The radiation source 5 provides radiation to the fiber 8 which transmits it to the sample by way of a jacket 18. A return fiber 8 is adjacent or abutting the first fiber at the sample interface and extends through the jacket 18 to the detector 6. The housing 12 also has an extendable leg 36 and controller 37 for pressing the housing 12 to the side surface 11.

Figure 10:
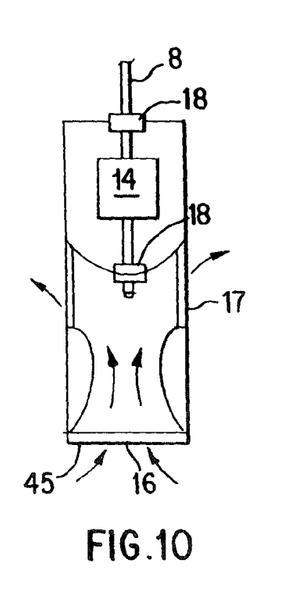
FIG. 10 shows a sectional view of an embodiment of the probe with a flow passage and fiber-optic tip as the sample interface.

FIG. 10 shows a fiber optic extending down the well and entering a housing 12 with a flow passage. A filter 14 or other dispersive elements are enclosed in the housing 12 and protected from the well environment. The fiber-optic tip 15 protrudes through a jacket 18 into the flow passage. The flow passage includes an inlet 16 with a filter 45 to filter particulates and other entrained material in the water and an outlet 17.

Figure 11:
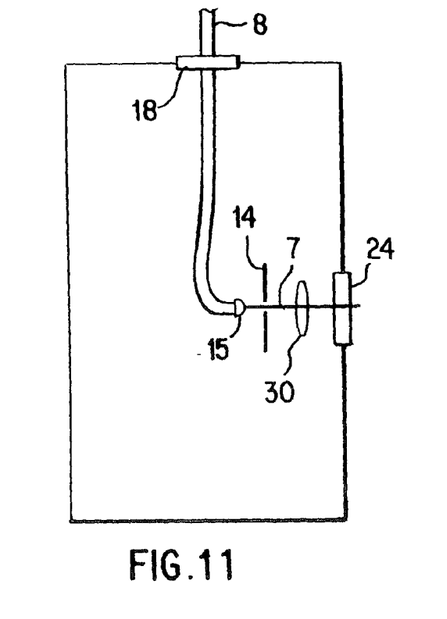
FIG. 11 shows a sectional view of an embodiment of the probe with a fiber-optic optical pathway.

FIG. 11 shows a fiber 8 optical pathway which enters the housing 12 and provides the transmitted radiation to a filter 14 or other dispersive element, lens 30 and window 24.

Optical spectrometers of utility for this method include, but are not limited to, Raman spectrometers, Fourier Transform Raman spectrometers, infrared (IR) spectrometers, Fourier Transform infrared spectrometers, near and far infrared spectrometers, Fourier Transform near and far infrared spectrometers, ultraviolet and visible absorption spectrometers, fluorescence spectrometers, and X-Ray spectrometers. All other spectroscopies which operate by observing the interactions and/or consequences of the interactions between naturally-occurring, deliberately-induced, and/or accidentally-induced light and matter are also of utility for this method.

For the spectrometer employing reflected, emitted or scattered characteristic radiation, a Raman spectrometer, a near IR spectrometer, a IR spectrometer, a UV/Vis spectrometer or fluorimeter is suitable for characterizing the side surface of the borehole.

Previously, using spectrometers to measure dissolved methane in water or embedded methane at a remote location like a wellhead was not thought possible. With the advent of portable and inexpensive yet highly accurate spectrometers, the measurement of dissolved methane in water is possible. In some cases the spectrum used to analyze the material of interest may be obscured or blocked to some extent by the medium in which it is found. In the case of coal bed methane, the water and entrained particles may cause significant interference with any measurement of the dissolved or embedded methane. Certain steps may be taken to ensure a more accurate analysis of the methane.

Data correction, filters and steps to improve the signal of the spectrometer and methane may be used to accurately measure the methane concentrations. Methane has a characteristic peak or peaks in the scattered or returned optical spectrum. By adjusting filters and any data correction equipment to the expected methane peak, the dissolved methane may be more accurately measured. Another way of correcting for the interference of water or other entrained material is to adjust or select the wavelength of the radiation used to decrease the effects of the water and entrained material and increase, the returned signal due to the methane. The wavelength may also be adjusted or selected to alleviate the effects of the length of the optical pathway. The length of the optical pathway from the spectrometer to the coal bed formation may be 10,000 feet. The great length of pathway will result in increased errors associated with the optical pathway. Means to adjust or correct the laser radiation or returned radiation from the sample may be employed at any location in the measurement system.

In an embodiment of this method, the spectrometers are physically located outside of the water, while sampling probes are introduced into the samples of interest. Such probes provide optical pathways via which interactions between light and matter are observed. In some cases, such probes also deliver the photons which interact with the matter. The probes used may have a lens to focus the source or characteristic radiation or filters to adjust the return spectrum radiation for any flaws in the system or extraneous signals. The probes may need armoring or other means for protecting the probe due to the pressure and other conditions of the well. The optical pathway or fiber optics may also need protection from the conditions of the well.

When the probe is located extreme distances from the spectrometer, such as down a well, corrections must be employed to correct for the inherent errors due to the distance the source radiation and spectrum radiation must travel. One way is to allow for longer periods of sampling in order to receive several spectrums added together to analyze the methane present. Another way is to adjust the signal or radiation through a filter or correction device to allow correction feedback to adjust the return spectrum for flaws and errors associated with the radiation traveling such distances.

In another embodiment of this method, the spectrometers are physically introduced into the water so as to be near the samples of interest. This manifestation provides an unexpected benefit in that delivery of photons to the samples and observation of interactions between light and matter are facilitated by the physical proximity of the spectrometers and the samples.

Both embodiments may also use error correction devices such as dark current subtractions of the return signal to correct for inherent system noise and errors. The systems may also use a technique of calibrating the source radiation and spectrum signal to assure an accurate methane concentration measurement. Such techniques may include data processing for comparing the signals to known spectrum signals. In order to calculate the concentration of methane any of the known techniques of calculating the concentration from a spectrum may be used. A preferred method is partial least squares or PLS to calculate concentrations.

In order to realize a preferred embodiment of this method, it is necessary to interface the spectrometers to the samples of interest. Interfacing the spectrometers and the samples can occur in several ways. Examples of those ways include, but are not limited to: direct optical coupling of the spectrometers and samples using light-guide devices; optical coupling of the spectrometers and chemicals which result from physically treating the samples; optically coupling of the spectrometers and chemicals which result from chemically treating the samples; and optically coupling of the spectrometers and chemicals which result from biologically treating the samples.

One manner of direct optical coupling of the spectrometers and samples using light-guide devices includes, but is not limited to, optical coupling of the interactions between light and matter via fiber optic devices. This manifestation provides an unexpected benefit in that delivery of photons to the samples and observation of interactions between light and matter occur with high throughput directly to the samples in some cases.

A preferred manner of optical coupling is by way of direct transmission of the radiation from the spectrometer to the sample via lenses, filters and/or windows, and the direct transmission of the characteristic radiation from the sample to the detector by way of filters, windows and/or lenses. This reduces the effects of long distance transmission through fiber optics and facilitates the close proximity of a spectrometer and sample.

The filters used may be placed along the optical pathways of the spectrometer. The filters or dispersive elements, collectively filters, may be wavelength selectors, bandpass filters, notch filters, linear variable filters, dispersive filters, gratings, prisms, transmission gratings, echelle gratings, photoacoustic slits and apertures.

In order for the spectrometers to withstand the conditions particular to wellbores, such as high pressure, low or high temperature, corrosive liquids and dissolved solids, for example, it is preferable to enclose the spectrometers in containers which protect them from such conditions. This novel method provides significant advantages over the prior art in that the enclosed spectrometers can then be introduced directly into the wellbore. This method allows, but does not require, realization of the benefit described by the direct interfacing or coupling of the samples and spectrometers.

In order to interface the spectrometers and the samples using such light-guide devices in the wellbore, it is necessary to design the interface in such a way that is suitable for the conditions particular to sampling environment, such as high pressure, low or high temperature, and dissolved solids, for example. The interface must withstand those and other conditions. One manifestation of such an interface for a fiber optic probe includes, but is not limited to, a high pressure feed-through jacket which interfaces between the conditions present in the enclosed spectrometer and those present in the wellbore. Such a jacket provides significant advantages in that using such a jacket direct optical coupling of the spectrometers to the samples becomes possible.

Methods of achieving optical coupling of the spectrometers and chemicals which result from physically treating samples includes, but is not limited to, introduction of the samples into a portion of the enclosed spectrometers. That portion is then physically affected so that treatment of the samples is achieved to give a chemical suitable for gas phase analysis via an optical pathway using one or more spectrometers. Such physical treatments include, but are not limited to, depressurization of the samples to release gas into a predefined ▓head-space▓ portion of the enclosure. That head space is then analyzed via optical pathways using one or more of the spectrometers. This method provides an unexpected benefit in that gas-phase energy spectra of chemicals are typically comprised of much higher resolution characteristics than the corresponding liquid-phase spectra. Thus, delineation of complex mixtures of gases, such as methane and water, is facilitated using this method.

The water located in the coal bed formation is considered to be stable or at equilibrium. The drilling of the well may agitate the water and may cause clouding or fouling of the water. In some circumstances the effects of the drilling and preparation of the well may be to artificially effect the concentration of the methane in the water and surrounding coal formations. Ways to correct the analyzed water may be employed to more accurately reflect the true methane concentration of the formation at equilibrium. A simple way is to allow the well to come back to an equilibrium after drilling or disturbance. Also, the probe or instrument package that contacts the water in the coal bed formation may be streamlined or controlled to allow for a smooth traverse in the water. The locations of measurement in the well may also alleviate the effects of destabilized water/methane concentrations. By analyzing the water at the top of the formation first, and then continue with measurements down the well will effect the water equilibrium less when measured before traversing the probe or package in the water to be analyzed. A filter may also be used to strain the water or sample.

In order to accurately predict the capacity and the production of a coal bed methane formation by optical analysis, the well must be drilled to an appropriate depth. The depth of the water table, if present, the depth of the top of the coal seam and the bottom of the coal seam are recorded. The well head must be prepared to receive the probe or instrument package. The probe must be coupled to the fiber-optic cable. The fiber-optic cable is coupled to the spectrometer that contains the light source, dispersion element, detector and signal processing equipment and ancillary devices. The computer that serves as an instrument controller, data collection and manipulation device is connected to the spectrometer system. The system (computer, spectrometer, detector and laser) are powered and the laser and operation equipment are allowed to reach an operating temperature. The detector is then cooled to operating temperature. The probe or instrument package is lowered into the well through the well head until the probe or package reaches the water table. The source or laser emits a radiation and the radiation is directed into the optical pathway or fiber-optic cable. The fiber-optic cable transmits the radiation down the well to the probe. The probe emits the radiation onto the sample of interest. The probe may contain a lens or lenses to focus the radiation onto the sample at different distances from the probe. The radiation interacts with the sample and causes the sample to reflect, scatter or emit a signature or characteristic radiation or spectrum. The spectrum or characteristic radiation is transmitted through the probe and optical pathway to the spectrometer. The spectrometer detects the spectrum or characteristic radiation and analyzes the spectrum for characteristic methane peaks or peak. The spectrometer then outputs information to the data processor to be manipulated into information to be used to calculate the concentration and potential production of methane.

During the analysis an initial spectrum is taken at the depth of the water table. The fluorescence is measured and, if the fluorescence is high, the source radiation wavelength may be adjusted or selected to mitigate the fluorescence. If particulates are present and the noise level from them is high, a different focal length may be chosen to mitigate the noise level. The integration time for the detectors is chosen to maximize the signal. A dark current spectrum is taken with the shutter closed such that no light reaches the detector. The dark current is the noise that is present in the system mostly due to thermal effects. This intensity is subtracted from each spectrum to lower the noise level. The number of co-additions is chosen to balance signal and time constraints. The co-additions will improve the signal to noise but will increase the time for each measurement. The probe or package is lowered to the top of the coal seam and a spectrum is taken. The probe is again lowered and a spectrum is taken at regular intervals of depth until the bottom of the well is reached. The measurements show a concentration of methane in accordance with depth in the well. By correlating the concentration of methane in the well with other data, the capacity of the coal bed formation or seam can be calculated. The probe is then retracted and the well head sealed.

This embodiment of the invention details the technical details surrounding the use of three different optical spectrometer systems capable of identifying and quantitatively analyzing coal bed methane formations. This embodiment centers around development of an instrument package capable of detecting the chemical signatures of dissolved methane and other gases in water and detecting embedded or trapped methane in subsurface coal seams, both from a lowered instrument package and from a fixed monitoring site. Such optic-based instruments are suitable for complex analysis of the physical and chemical properties of dissolved methane and similar formations in the wellbore environments.

In these cases, the instruments themselves are packaged and adapted to the conditions prevalent in these environments, and the formations are examined in the natural state or after suitable treatment. This provides direct access to the chemistry and geology of the formations to an extent unavailable from core-sampling techniques.

At least three types of spectrometers are suitable for wellbore remote sensing of methane. The first two spectrometers, UV/Vis and near IR, are particularly suitable for head-space sensing of gases released after depressurization of the coal bed samples. UV/Vis spectroscopy provides data relating to the molecular absorption properties of the water. Depending on experimental concerns, this data may contain information regarding the identity and concentration of dissolved hydrocarbon gases. Regardless, though, it contains information related to choosing the proper laser excitation wavelength for the Raman spectrometer. Near infrared (NIR) spectroscopy has been widely used to remotely characterize complex gas mixtures. In this case, the NIR spectrometer provides data related to the structure and bonding of the gas samples. If the spectrometer resolution is sufficient, that data contains sufficient information to allow deconvolution of very complex samples.

Both of the above spectrometers require substantial fluid handling to be integrated into the sensor or instrument package. This results in slower collection times and, for the lowered instrument package, a lower spatial resolution for the data, when compared to directly coupled in-situ methods. On the other hand, Raman spectroscopy is performed using state-of-the-art high-pressure probes, allowing rapid chemical analysis of water and methane with no additional hardware.

Raman spectroscopy detects the identity and concentration of dissolved hydrocarbon gases and embedded hydrocarbon gases. The Raman scattering of typical materials is quite low, producing significant signal-to-noise problems when using this type of spectroscopy. However, symmetric molecules including methane show very strong scattering. This moderates signal-to-noise concerns to some extent.

Again, all three spectrometers are refitted to suitable pressure tube specifications. The tube-bound spectrometers will be immersed to suitable depths on available well equipment or located adjacent the well, and the data is collected using existing data translation protocols. The data bandwidth for all three instruments is relatively low ca. 50 KB per minute is a reasonable rate (dependent to some extent on the signal-to-noise concerns).

UV/Vis Spectrometer

Because UV/Vis spectrometers are based on low intensity, white light sources, the use of focused optic probes (such as fiber optics) in this case is not appropriate. Such spectrometers are more suited to gas analysis of the head space created after depressurization of a sample. Thus, in order to use the UV/Vis spectrometer for methane analysis, mechanized fluid controls are preferred.

An automated fluid decompression chamber that can be filled, depressurized, analyzed, and evacuated on a continual basis at the well depth of interest is provided. Depressurization of the chamber releases the dissolved hydrocarbon gases into the resultant vacuum where they are efficiently and quickly analyzed by the UV/Vis spectrometer. Evacuation and flushing of the chamber is followed by another cycle.

Some issues of concern using this type of spectrometer are developing the appropriate optical path for analysis, avoiding fouling of the chamber and optical windows by water-borne chemicals and bio-organisms, and establishing the appropriate temperature/pressure conditions for data collection. Corresponding solutions are multiple reflection collection geometries which afford very high sensitivities, proper introduction of anti-foulants to the chamber during flushing, and laboratory correlation of the entire range of available pressure/temperature collection conditions to resulting data quality.

Doing such head-space analysis also provides a convenient method for the sensor platform to analyze chemically gas bubbles resulting from dissolution, cavitation or mixing, which would not otherwise be suitable for analysis. For example, diversion of captured gas into the head-space through appropriate valves provides the opportunity for direct UV/Vis and NIR analysis of the emitted gases.

Near IR Spectrometer

Near IR and Raman spectrometers detect the identity (i.e. molecular bonding) and concentration of dissolved and embedded hydrocarbon gases. Near IR analysis, widely used for quality control in industrial processes, typically gives moderate signals with sufficient information (i.e. overtones of the vibrational bands) to treat very complicated samples. Near IR spectrometers may be used for head-space analysis. Allowing multiple reflections of the beam through the cell (and thus multiple passes of the beam through the sample) provides the unexpected benefit of increasing the signal-to-noise ratio of the data. Direct optical coupling of near IR spectrometers to the samples is also preferred.

Raman Spectrometer

Raman spectroscopy is widely used for in-situ analysis of water-borne samples because water does not have a strong interaction with typical Raman laser energies. The Raman spectrometer is based on traditional grating optics, and thus enjoys a high throughput of light.

Spectroscopic capabilities are maximized by, in some cases, using a fiber-optic probe sampling motif based around a filtered, six-around-one fiber-optic probe. The six-around-one fiber-optic probe allows for a safe, fully-sealed optical feed-through from the pressure vessel to the water. This design removes the elaborate fluidics necessary for the other two spectrometers.

Until recently Raman spectroscopy would never have been considered as an in-situ probe due to the large size of available Raman systems and their high power consumption. High efficiency diode lasers and charge-coupled device (CCD) detection, along with better filter technology have made it possible to miniaturize Raman spectrometers and decrease power consumption. Fiber-optic probes have eliminated the complex sampling arrangements that once made Raman spectroscopy difficult and tedious.

A long output wavelength often provides useful spectra from samples that produce interfering fluorescence at lower wavelengths. Even at these longer wavelengths, inorganic vibration shifts that are commonly 400 to 1000 cm-1 wave numbers shifted in wavelength are still near the peak sensitivity of CCD detectors but with the added advantage of a significant reduction in the background fluorescence interference present in many samples. A preferred embodiment uses laser wavelengths which avoid to a reasonable extent any fluorescence characteristic of the sample.

Usually fluorescence is mitigated by providing a laser with a wavelength above the fluorescence. In a preferred embodiment a wavelength of 450 nm to 580 nm is provided from a diode laser. This range is below the wavelength of fluorescence of coal. The shorter wavelength is used to decrease the radiation from the coal and increase the relative radiation from the methane embedded or adsorbed on the coal.

Remote sampling is accomplished in some cases using a six-around-one probe. The epi-illumination probe incorporates one excitation and six collection fibers. This probe allows direct measurement of Raman of dissolved hydrocarbons in water without having to transmit through thick, non-quality optical window ports. High pressure feed-throughs are available for this probe.

Measurements of spectroscopic signatures of water-dissolved hydrocarbons in the laboratory show an energy diagram of the known spectroscopic signature regions of simple hydrocarbons, and the regions interrogated by the three spectrometers considered herein. Thus, all three spectroscopies provide information relevant to the hydrocarbon identity and concentration.

However, the UV/Vis bands typical for these hydrocarbons are NOT strongly characteristic many compounds absorb in the energy region between 0 and 250 nm. Correlation of the UV/Vis results with those from the Raman and/or near IR leads to detailed chemical analysis. As well, the UV spectrometer must operate in the region where the methane transition occurs.

The detectors used with the spectrometer system are important. To obtain high sensitivity and reduce interference from other substances a CCD type detector is preferred. The charge-coupled device detector allows for only a small portion of the spectrum to be analyzed. Other detectors include photomultiplier tubes, photo-diode arrays, CMOS image sensors, avalanche photo diodes and CIDs.

The measuring system may be supplied with power by the guide wires or by internal batteries.

In order to predict or measure a potential production from a coal bed methane field, a series of wells is measured. Taking measurements of methane or other substances of interest at a single well and at varying depths down the well provides a concentration of methane versus depth for the well. This indicates the presence and amount of methane in the subsurface zones or strata. By similarly measuring other wells in the coal bed methane formation or field a dimensional plot of methane is obtained. From this the transport of methane, production zones and extent of methane bearing zones is obtained.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

We claim:

1. A method of measuring methane using a spectrometer in a coal bed methane well with a borehole extending to at least a top surface of at least one coal bed and containing water, comprising:

providing a housing including a radiation source, a detector and a sample interface, lowering the housing in the coal bed methane well to a depth down the well, positioning the sample interface to a sample located outside of the housing, irradiating the sample from the radiation source, detecting a characteristic radiation from the sample with the detector of the spectrometer, and processing a signal from the detector to calculate a concentration of the methane.

2. A method of measuring according to claim 1, wherein the sample is a face of the coal bed.

3. A method of measuring according to claim 2, wherein the radiation source is selected to minimize a radiation from the coal.

4. A method of measuring according to claim 2, wherein a wavelength of the radiation source is lower than a wavelength producing maximum fluorescence in the coal.

5. A method of measuring according to claim 1, wherein the characteristic radiation is emitted, reflected or scattered radiation.

6. A method of measuring according to claim 1, wherein the sample is a volume of water in the well at or near the depth down the well.

7. A method of measuring according to claim 1, wherein the sample is a collected gas from the water which has been depressurized to release the gas.

8. A method of measuring according to claim 1, wherein the sample is chemically treated before the irradiating.

9. A method of measuring according to claim 1, wherein the sample is biologically treated before the irradiating.

10. A method of measuring according to claim 1, wherein the radiation source is selected to minimize fluorescence.

11. A method of measuring according to claim 1, wherein the sample interface includes at least one lens to focus the radiation from the radiation source, and a focal length of the sample interface is adjusted to mitigate a noise level or to increase the detected characteristic radiation.

12. A method of measuring according to claim 1, wherein the radiation source is a tunable laser located in the housing.

13. A method of measuring according to claim 1, wherein the radiation source is a diode laser with a wavelength between 450 nm and 580 nm.

14. A method of measuring according to claim 1, wherein the detector is an optical fiber transmitting the characteristic radiation to a charge-coupled device.

15. A method of measuring methane in at least one coal bed methane well, comprising:
providing an instrument package in a housing,
lowering the housing to a depth down the coal bed methane well,
positioning a radiation source to irradiate a sample and a detector to detect a characteristic radiation from the sample,
irradiating the sample which is located outside the housing with radiation from the radiation source to produce the characteristic radiation from the sample, and
measuring a concentration of methane in the sample by detecting the characteristic radiation from the sample with the detector, transmitting a signal from the detector to a signal processor and processing the signal to calculate the concentration of the methane in the sample.

16. A method of measuring according to claim 15, wherein the radiation source includes an optical fiber transmitting light waves from a spectrometer near a well head and connected to the housing.

17. A method according to claim 15, further comprising:
lowering the package to at least a second depth down the well, and measuring a concentration of methane at the second depth, in order to obtain concentration of methane versus depth of the well.

18. A method according to claim 15, further comprising:
obtaining concentration of methane versus depth of at least a second well, in order to obtain a potential production of a coal formation.

19. A method according to claim 15, wherein the instrument package is sealed against water and armored to withstand pressure down the well.

20. A method according to claim 15, wherein the package includes a radiation source for supplying a radiation to irradiate the sample.

21. A method according to claim 15, wherein the package includes the detector for detecting the characteristic radiation from the sample and transmitting the signal.

22. A method according to claim 21, wherein the package includes the signal processor for processing the signal from the detector.

23. A method according to claim 15, wherein the package includes a filter for filtering the radiation from the radiation source.

24. A method according to claim 15, wherein the package includes a filter for filtering the characteristic radiation before the detector.

25. A method according to claim 15, wherein the radiation source is a diode laser at a wavelength which minimizes a fluorescence of the coal.

26. A method according to claim 15, wherein the depth is at a top of a water column in the well.

27. A method according to claim 15, wherein the depth is at a top of a first coal bed.

28. A method according to claim 15, wherein the depth is at a top of a second coal bed.

29. A method according to claim 15, wherein the sample is water at or near the depth.

30. A method according to claim 15, wherein the sample is a bacterium or bacterial community.

31. A method according to claim 15, wherein the housing includes at least one window for transmitting the radiation from the radiation source and the characteristic radiation.

32. A method according to claim 31, wherein the window is positioned next to the sample.

33. A method according to claim 15, wherein the sample is a face of the wellbore.

34. A method according to claim 33, wherein a portion of the housing is pressed into the face of the wellbore.

35. A method according to claim 33, wherein the face of the wellbore is scraped or prepared to provide a sampling surface.

36. A method according to claim 15, wherein the sample is a face of the coal bed.

37. A method according to claim 15, further comprising selecting a wavelength of the radiation source to mitigate fluorescence.

38. A method according to claim 37, wherein the wavelength is selected to mitigate a radiation from entrained particles in the water.

39. A method according to claim 37, wherein the wavelength is selected to mitigate errors due to length of optical pathways transmitting the radiation from the radiation source and the characteristic radiation.

40. A measuring system for introduction into a well, comprising:
a housing being traversable up and down the well,
a guide extending down the well from a fixed location and being operatively connected to the housing,
a spectrometer being located inside the housing and including a radiation source, a sample interface to transmit a radiation from the radiation source to a sample located outside of the housing, and a detector to detect a characteristic radiation from the sample and to output a signal, and
a signal processor to process the signal from the detector and calculate a concentration of a substance in the sample.

41. A measuring system according to claim 40, wherein the probe has no moving parts.

42. A measuring system for in-situ measurements down a well with a borehole by a spectrometer, comprising:
the spectrometer including a radiation source and a detector,
a probe being optically connected to the spectrometer and including an optical pathway for transmission of a radiation from the radiation source and at least a second optical pathway for transmission of a characteristic radiation from a sample to the detector, and a positioner to position the probe near a side surface of the borehole and to optically couple the optical pathways to the side surface of the borehole, wherein the sample is located outside of the probe, and wherein the probe is traversable up and down the well by way of a guide.

43. A measuring system according to claim 42, wherein the sample is methane adsorbed to coal.

44. A measuring system according to claim 42, wherein the optical pathway for transmission of the radiation from the radiation source includes at least one lens for focusing the radiation from the radiation source onto the sample.

45. A measuring system according to claim 42, wherein the positioner includes an adjustable device which extends from the probe and presses a side of the wellbore.

46. A measuring system according to claim 42, wherein the radiation source is a diode laser at a wavelength of 450 nm to 580 nm.

47. A measuring system according to claim 42, wherein a filter is located between the radiation source and the sample to filter the radiation from the radiation source.

48. A measuring system according to claim 42, wherein at least one filter is located between the sample and the detector to filter the characteristic radiation.

49. A measuring system according to claim 42, wherein the probe includes the spectrometer.

50. A measuring system according to claim 49, wherein the probe is armored against pressure and sealed against liquids.

51. A measuring system according to claim 49, wherein the probe includes a high-pressure feed-through jacket for an optical fiber which interfaces between the enclosed spectrometer and the wellbore.

52. A measuring system according to claim 49, wherein the probe includes a reflector to direct the radiation from the radiation source to the sample and a second reflector to direct the characteristic radiation from the sample to the detector.

53. A measuring system according to claim 42, wherein an error corrector is provided to correct for inherent system noise and errors.

54. A measuring system according to claim 42, wherein the probe is optically connected to the radiation source via at least one optical fiber.

55. A measuring system according to claim 42, wherein the probe is optically connected to the detector via at least one optical fiber.

56. A measuring system according to claim 42, wherein the probe is streamlined so as not to substantially disturb the water in the well.

57. A measuring system according to claim 42, wherein the radiation source is a UV/Vis spectrometer.

58. A measuring system according to claim 42, wherein the radiation source is a near IR spectrometer.

59. A measuring system according to claim 42, wherein the radiation source is a Raman spectrometer.

60. A measuring system according to claim 42, wherein the radiation source is an infrared spectrometer.

61. A measuring system according to claim 42, wherein the radiation source is a fluorimeter.

62. A measuring system according to claim 42, wherein the detector is a charge-coupled device.

63. A measuring system according to claim 42, wherein the detector includes at least one of a photomultiplier tube, a photo-diode array, an avalanche photo-diode, a charge injection device and a complimentary metal-oxide semiconductor image sensor.

64. A method of measuring a side surface of a borehole using an optical spectrometer, comprising:

providing the optical spectrometer including a radiation source and a detector, optically connecting the side surface of the borehole to the radiation source and the detector, said side surface being located outside of the spectrometer, irradiating the side surface of the borehole with radiation from the radiation source, collecting a characteristic radiation from an interaction between the side surface of the borehole and the radiation from the radiation source, transmitting the characteristic radiation to the detector to thereby produce a signal, transmitting the signal to a signal processor, and calculating a concentration of a substance on the side surface of the borehole.

65. A method according to claim 64, wherein the side surface of the borehole is a face of a coal seam.

66. A method according to claim 64, wherein the side surface is optically connected by at least one lens which focuses the radiation from the radiation source onto the side surface.

67. A method according to claim 64, wherein the side surface is optically connected to the radiation from the radiation source by at least one fiber optic which is positioned near the side surface.

68. A method according to claim 67, wherein the fiber optic is pressed into the side surface.

69. A method according to claim 64, wherein the side surface is optically connected to the radiation from the radiation source via a window or lens in a housing.

70. A method according to claim 69, wherein the housing is pressed into the side surface.

71. A method according to claim 69, wherein the housing is lowered down the wellbore and is positioned near the side surface by an adjustable device extending from the housing.

72. A method according to claim 69, wherein the spectrometer is located in the housing.

73. A method according to claim 64, wherein the radiation source is a diode laser with a wavelength between 450 nm and 580 nm.

* * * * *